(12) United States Patent
Tammero et al.

(10) Patent No.: US 8,762,068 B2
(45) Date of Patent: Jun. 24, 2014

(54) METHODS FOR THRESHOLD DETERMINATION IN MULTIPLEXED ASSAYS

(75) Inventors: Lance F. Bentley Tammero, Oakland, CA (US); John M. Dzenitis, Danville, CA (US); Benjamin J. Hindson, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 460 days.

(21) Appl. No.: 12/607,956

(22) Filed: Oct. 28, 2009

(65) Prior Publication Data
US 2011/0021368 A1    Jan. 27, 2011

Related U.S. Application Data

(60) Provisional application No. 61/228,499, filed on Jul. 24, 2009.

(51) Int. Cl.
| | |
|---|---|
| G06F 19/24 | (2011.01) |
| G06F 19/20 | (2011.01) |
| C12Q 1/68 | (2006.01) |
| G01N 33/53 | (2006.01) |
| G06K 9/62 | (2006.01) |
| G01N 33/569 | (2006.01) |
| G01N 35/00 | (2006.01) |

(52) U.S. Cl.
CPC ............ *G06F 19/24* (2013.01); *G06F 19/20* (2013.01); *C12Q 1/6813* (2013.01); *C12Q 1/6851* (2013.01); *C12Q 1/6888* (2013.01); *C12Q 2537/143* (2013.01); *C12Q 2537/165* (2013.01); *G01N 33/53* (2013.01); *G01N 33/569* (2013.01); *G01N 35/00613* (2013.01); *G01N 35/00693* (2013.01); *G06K 9/626* (2013.01); *G06K 9/6217* (2013.01)
USPC ................ 702/19; 435/6.1; 435/7.1

(58) Field of Classification Search
None
See application file for complete search history.

(56) References Cited

U.S. PATENT DOCUMENTS

| | | | |
|---|---|---|---|
| 5,624,802 A | | 4/1997 | Urdea et al. |
| 2005/0239116 A1* | | 10/2005 | Willey .............................. 435/6 |

OTHER PUBLICATIONS

Hindson, B. J. et al. Diagnostic evaluation of multiplexed reverse Transcription—PCR microsphere array assay for detection of Foot-and-Mouth and Look-Alike disease viruses. Journal of Clinical Microbiology 46, 1081-1089 (2008).*

Massart, D. L., Vandeginste, B. G. M., Deming, S. N., Michotte, Y. & Kaufman, L. Chemometrics: A Textbook. (Elsevier Science B.V., 1988). Excerpt of chapter 5 ("Calibration") and chapter 7 ("Sensitivity and Limit of Detection").*

Desimoni, E., Brunetti, B. & Cattaneo, R. Comparing Some Operational Approaches to the Limit of Detection. Ann. Chim. 94, 555-569 (2004).*

(Continued)

*Primary Examiner* — Soren Harward
(74) *Attorney, Agent, or Firm* — Steinfl & Bruno, LLP

(57) ABSTRACT

Methods for determination of threshold values of signatures comprised in an assay are described. Each signature enables detection of a target. The methods determine a probability density function of negative samples and a corresponding false positive rate curve. A false positive criterion is established and a threshold for that signature is determined as a point at which the false positive rate curve intersects the false positive criterion. A method for quantitative analysis and interpretation of assay results together with a method for determination of a desired limit of detection of a signature in an assay are also described.

15 Claims, 8 Drawing Sheets

(56) References Cited

OTHER PUBLICATIONS

Gibbons, R. D., Coleman, D. E. & Maddalone, R. F. An Alternative Minimum Level Definition for Analytical Quantification. Environ. Sci. Technol. 31, 2071-2077 (1997).*
Lavagnini, I., Antiochia, R. & Magno, F. A Calibration-Base Method for the Evaluation of the Detection Limit of an Electrochemical Biosensor. Electroanalysis 19, 1227-1230 (2007).*
Lavagnini, I. & Magno, F. A statistical overview on univariate calibration, inverse regression, and detection limits: Application to gas chromatography/mass spectrometry technique. Mass Spectrom. Rev. 26, 1-18 (2007).*
Zorn, M. E., Gibbons, R. D. & Sonzogni, W. C. Weighted least-squares approach to calculating limits of detection and quantification by modeling variability as a function of concentration. Anal. Chem. 69, 3069-3075 (1997).*
Thompson, D.; Muriel, P.; Russell, D.; Osborne, P.; Bromley, A.; Rowland, M.; Creigh-Tyte, S.; Brown, C. Rev. Sci. Tech. Off. Int. Epiz. 2002, 21, 675-687.
Bourn, J. Department for environment, food and rural affairs, National Audit Office, U.K., pp. 1-61, 2005.
Kitching, R. P.; Hutber, A. M.; Thrusfield, M. V. Veterinary Journal 2005, 169, 197-209.
Reid, S. M.; Panda, S.; King, D. P.; Hutchings, G. H.; Shaw, A. E.; Ferris, N. P.; Zhang, Z. D.; Hillerton, J. E.; Paton, D. J. Vet. Res. 2006, 37, 121-132.
Zhang, Z. D.; Alexandersen, S. J. Virol. Methods 2003, 111, 95-100.
Callahan, J. D.; Brown, F.; Csorio, F. A.; Sur, J. H.; Kramer, E.; Long, G. W.; Lubroth, J.; Ellis, S. J.; Shoulars, K. S.; Gaffney, K. L.; Rock, D. L.; Nelson, W. M. J. Am. Vet. Med. Assoc. 2002, 220, 1636-1642.
Reid, S. M.; Ferris, N. P.; Hutchings, G. H.; Zhang, Z. D.; Belsham, G. J.; Alexandersen, S. J. Virol. Methods 2002, 105, 67-80.
Oleksiewicz, M. B.; Donaldson, A. I.; Alexandersen, S. J. Virol. Methods 2001, 92, 23-35.
Letellier, C.; Kerkhofs, P. J. Virol. Methods 2003, 114, 21-27.
Bhudevi, B.; Weinstock, D. Vet. Microbiol. 2001, 83, 1-10.
Baxi, M.; McRae, D.; Baxi, S.; Greiser-Wilke, I.; Vilcek, S.; Amoako, K.; Deregt, D. Vet. Microbiol. 2006, 116, 37-44.
Johnson, D. J.; Wilson, W. C.; Paul, P. S. Vet. Microbiol. 2000, 76, 105-115.
Jimenez-Clavero, M. A.; Aguero, M.; Miguel, E. S.; Mayoral, T.; Lopez, M. C.; Ruano, M. J.; Romero, E.; Monaco, F.; Polci, A.; Savini, G.; Gomez-Tejedor, C. J. Vet. Diagn Invest. 2006, 18, 7-17.
Nitsche, A.; Buttner, M.; Wilhelm, S.; Pauli, G.; Meyer, H. Clin. Chem. 2006, 52, 316-319.
Wilson, W. J.; Erler, A. M.; Nasarabadi, S. L.; Skowronski, E. W.; Imbro, P. M. Mol. Cell. Probes 2005, 19, 137-144.
Dunbar, S. A. Clin. Chim. Acta 2006, 363, 71-82.
Yan, X. M.; Zhong, W. W.; Tang, A. J.; Schielke, E. G.; Hang, W.; Nolan, J. P. Anal. Chem. 2005, 77, 7673-7678.
Hindson, B. J.; McBride, M. T.; Makarewicz, A. J.; Henderer, B. D.; Setlur, U. S.; Smith, S. M.; Gutierrez, D. M.; Metz, T. R.; Nasarabadi, S. L.; Venkateswaran, K. S.; Farrow, S. W.; Colston, B. W.; Dzenitis, J. M. Anal. Chem. 2005, 77, 284-289.
Perkins, J.; Clavijo, A.; Hindson, B. J.; Lenhoff, R. J.; McBride, M. T. Anal. Chem. 2006, 78, 5462-5468.
Fitch, J. P. Evolutionary Theories of Detection. DHS IEEE Conference, Boston MA, Apr. 25-28, 2005. UCRL CONF-212194. http://www.llnl.gov/tid/lof/documents/pdf/319757.pdf.
Zweig, M. H.; Campbell, G. Clin. Chem. 1993, 39, 561-577.
Greiner, M.; Pfeiffer, D.; Smith, R. D. Prev. Vet. Med. 2000, 45, 23-41.
Greiner, M.; Sohr, D.; Gobel, P. J. Immunol. Methods 1995, 185, 123-132.
Dunbar, S.A., Vander Zee, C.K., Oliver, K.G., Karem, K.L., Jacobson, J.W., 2003. Quantitative, multiplexed detection of bacterial pathogens: DNA and protein applications of the Luminex LabMAP system. Journal of Microbiological Methods 53, 245-252.
Finney, D.J., 1978. Statistical Methods in Biological Assays, 3rd ed. MacMillan Publishing Co., Inc., New York, NY, pp. 394-398 (Assays based on quantal responses).
Flint, S.J., Enquist, L.W., Racaniello, V.R., Skalka, A.M., 2004. Principles of Virology Molecular Biology, Pathogenesis, and Control of Animal Viruses, 2nd ed. ASM Press, Washington, DC, p. 35.
Haydon, D.T., Bastos, A.D.S., Awadalla, P., 2004. Lowlinkage disequilibrium indicative of recombination in foot-and-mouth disease virus gene sequence alignments. Journal of General Virology 85, 1095-1100.
Hietala, S., Crossley, B., 2006. Armored RNA as virus surrogate in a real-time reverse transcriptase PCR assay proficiency panel. Journal of Clinical Microbiology 44, 67-70.
Kellar, K.L., Iannone, M.A., 2002. Multiplexed microsphere-based flow cytometric assays. Experimental Hematology 30, 1227-1237.
McBride, M.T., Gammon, S., Pitesky,M., O'Brien, T.W., Smith, T., Aldrich, J., Langlois, R., Venkateswaran, K.S., 2003. Multiplexed liquid arrays for simultaneous detection of simulants of biological-warfare agents. Analytical Chemistry 75, 1924-1930.
Reed, L.J., Muench, L.H., 1938. A simple method of estimating fifty percent endpoints. American Journal of Hygiene 27, 493-497.
Reid, S.M., King, D.P., Shaw, A.E., Knowles, N.J., Hutchings, G.H., et al., 2006. Development of a real-time reverse transcription polymerase chain reaction assay for detection of marine caliciviruses (genus *Vesivirus*). Journal of Virological Methods 140, 166-173.
Ripa, T., Nilsson, P.A., 2007. A *Chlamydia trachomatis* strain with a 377-bp deletion in the cryptic plasmid causing false-negative nucleic acid amplification tests. Sexually Transmitted Diseases 35, 255-256.
Rweyemamu, M.M., Astudillo, V.M., 2002. Foot and mouth disease: facing the new dilemmas. Revue Scientifique et Technique de I Office International des Epizooties 21, 765-773.
Scudmore, J.M., Trevelyan, G.M., Tas, M.V., Varley, E.M., Hickman, G.A., 2002. Carcass disposal: lessons from Great Britain following the foot and mouth disease outbreaks of 2001. Revue Scientifique et Technique 21, 775-787.
Slezak, T., Kuczmarski, T., Ott, L., Torres, C., Medeiros, D., et al., 2003. Comparative genomics tools applied to bioterrorism defense. Brief Bioinformatics 4, 133-149.
Restriction Requirement for U.S. Appl. No. 12/698,785, filed Feb. 2, 2010 in the name of Lance F. Bentley Tammero et al. Mail Date: May 24 2012.
Non-Final Office Action for U.S. Appl. No. 12/698,785, filed Feb. 2, 2010 in the name of Lance F. Bentley Tammero et al. Mail Date: Aug. 2, 2012.
Notice of Allowance for U.S. Appl. No. 12/698,785, filed Feb. 2, 2010 in the name of Lance F. Bentley Tammero et al. Mail Date: Feb. 28, 2013.

* cited by examiner

METHODS FOR THRESHOLD DETERMINATION IN MULTIPLEXED ASSAYS

STATEMENT OF GOVERNMENT GRANT

The U.S. Government has certain rights in this invention pursuant to Contract No. W-7405-ENG-48 between the U.S. Department of Energy and the University of California.

CROSS REFERENCE TO RELATED APPLICATIONS

The present application claims priority to U.S. Prov. App. No. 61/228,499 filed on Jul. 24, 2009 and incorporated herein by reference in its entirety.

FIELD

The present disclosure relates to assays. In particular, the present disclosure relates to threshold determination for interpretation of arrays, e.g., multiplexed assays.

BACKGROUND

Multiplexed assays are used in several fields of technology to simultaneously detect multiple targets (e.g., dozens or more) in a single procedure where the presence and/or the activity of the targets is determined quantitatively or qualitatively.

Multiplexed assay detection is typically performed by measuring a signal, such as fluorescence and chemoluminescence, and determining the outcome of the assay based on the position of the detected signal with respect to a predetermined threshold.

In particular, the interpretation of the results of a multiplexed assay typically begins by comparing a raw response to a threshold value. Signal detection theory has been used to describe the effect of varying threshold value on assay performance [see references 15, 16]. An ideal threshold value completely separates positive sample responses from negative sample responses In practice, however, distributions of responses generated by positive and negative samples can overlap. When overlap occurs, the number of both true positives (positive samples exceeding threshold) and false positives (negative samples exceeding threshold) increases as the threshold value decreases.

Therefore, accurate interpretation of multiplexed assays is currently a challenging task, in particular with reference to the correct determination of quantitative detection of multiple targets.

SUMMARY

Provided herein, are methods that in several embodiments can be used for an accurate interpretation of multiplexed assays.

According to a first aspect, a method for determination of threshold values of signatures comprised in an assay is provided, each signature enabling detection of a target, the method comprising, for each signature: determining a probability density function (PDF) of negative samples; based on the determined PDF of negative samples, determining a false positive rate curve; establishing a false positive criterion; and determining a threshold for that signature as a point at which the false positive rate curve intersects the false positive criterion.

The methods herein described can be used, in several embodiments, to quantify the performance and limitations of all microarray based assays, in particular those performed using the Luminex® suspension array. A microarray assay is a multiplex assay where multiple ligands (such as DNA oligonucleotides or proteins or antibodies) are bound to a synthetic series of probes. As an alternative to the Luminex suspension array, an Affymetrix® chip can be used, comprising a number of probes bound to a silicon chip, or a BeadArray® (made by Illumina, Inc.) which comprises a high-density microwell array connected to individual optical fibers.

In particular, in several embodiments, the methods herein described can be applied to any assay during which a response parameter, such as a median or mean fluorescence intensity (or other statistical measure related to fluorescence intensity) is determined.

The methods herein described can be used in connection with performance of bio-assays in field such as biological agents analysis, medical clinical diagnostics, and analysis of agricultural samples. According to other embodiments of the present disclosure, the teachings of the present disclosure can be used with assays that measure quantities other than biological quantities, such as testing for the presence of chemicals.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

DETAILED DESCRIPTION

Figure 1:
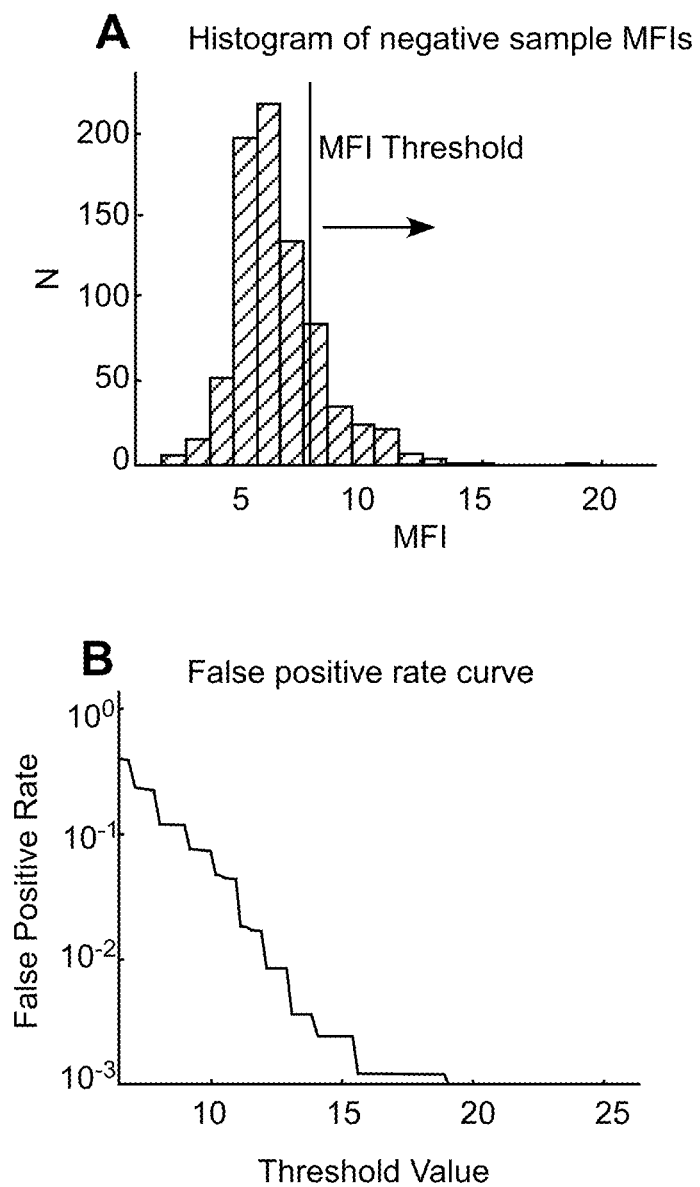
FIG. 1 shows an assay response distribution according to an embodiment described herein. An example histogram of blank median fluorescent intensity (MFI) responses is plotted (panel A), along with an indicated MFI threshold value. A sample receiver operator characteristic (ROC) function is plotted in panel B.

Provided herein, are methods that in several embodiments can be used for interpretation of multiplexed assays, and in particular for quantitative interpretation of multiplexed assays.

The term "assay" as used herein indicates a procedure for detecting a target in an organism or organic sample. The term "detect" or "detection" as used herein indicates the determination of the existence, presence or fact of a target or signal in a limited portion of space, including but not limited to a sample, a reaction mixture, a molecular complex and a substrate. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified. Bioassays and immunoassays are among the many varieties of assays directed to detection of targets of biological and/or chemical interest. Additional exemplary assays detect targets related to such processes as enzyme activity, antigen capture, stem cell activity, and competitive protein binding.

Detection of targets can be typically performed by using "signatures" i.e. capture agents comprising an oligonucleotide sequence designed to bind a desired target used in combination with suitable labels and/or labeled molecule.

The term "capture agent" or "captor" as used herein indicates a compound that is able to specifically bind a target wherein the terms "specific" "specifically" or specificity" as used herein with reference to the binding of a molecule to another refers to the recognition, contact and formation of a stable complex between the molecule and the another, together with substantially less to no recognition, contact and formation of a stable complex between each of the molecule and the another with other molecules. Exemplary specific bindings are antibody-antigen interaction, cellular receptor-ligand interactions, polynucleotide hybridization, enzyme substrate interactions etc.

The terms "label" and "labeled molecule" as used herein as a component of a complex or molecule refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like.

The term "fluorophore" refers to a substance or a portion thereof which is capable of exhibiting fluorescence in a detectable image.

As a consequence the wording "labeling signal" as used herein indicates the signal emitted from the label that allows detection of the label, including but not limited to radioactivity, fluorescence, chemolumiescence, production of a compound in outcome of an enzymatic reaction and the likes. Exemplary signatures are provided by two primers and a probe that specifically bind a specific genetic sequence. Other examples might include labeling via the bonding between antigen and antibodies.

The term "target" as used herein indicates an analyte of interest. The term "analyte" refers to a substance, compound or component whose presence or absence in a sample has to be detected. Analytes include but are not limited to biomolecules and in particular biomarkers. The term "biomolecule" as used herein indicates a substance compound or component associated to a biological environment including but not limited to sugars, aminoacids, peptides proteins, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state. The presence, absence, reduction, upregulation of the biomarker is associated with and is indicative of a particular state.

The term "sample" as used herein indicates a limited quantity of something that is indicative of a larger quantity of that something, including but not limited to fluids from a biological environment, specimen, cultures, tissues, commercial recombinant proteins, synthetic compounds or portions thereof.

The term "interpretation" as used herein indicates is a set of one or more statements constructed to describe a set of facts which indicates the causes, context, and/or consequences of those facts. Accordingly, the wording "Quantitative interpretation" as used herein indicates a set of one or more statements constructed to describe a set of facts related to quantitative performance in the detection of a target.

In several embodiments, the methods herein described can be used in addition or in place of other methods for quantitative interpretation of multiplexed assays and in particular of multiplexed array assays, including but not limited to assays for the detection of DNA segments or antigens, and other assays which are identifiable by a skilled person upon reading of the present disclosure. More particularly, in some embodiments, the methods herein described can be used for the quantitative analysis and interpretation of multiplexed liquid array assay results.

In methods and systems herein described, threshold values can be established for signatures used in an assay. The term "threshold" as used herein indicates a value above which a response is ruled positive. An example of a threshold would be a specific MFI value that needs to be exceeded for an assay to be ruled positive.

In several embodiments, a threshold value for at least one signature used in the assay for detection of a target can be determined by first determining a probability density function (PDF) of negative samples.

In particular, in some embodiments, obtaining the PDF of negative samples is performed by performing the assay on a number of negative samples and selecting the rate at which negative samples are rejected. In particular, this step can be performed by measuring the median fluorescence intensity (MFI) of each signature for a large number (e.g. about 1000) of negative samples (see, for example, Step 1 in the examples section) and generating a histogram (described, for example, in Step 2 of the examples section) describing the distribution of the resulting MFI values for each individual signature (FIG. 1A).

The term "median fluorescence intensity" or "MFI" as used herein indicates the density of specific molecules on the surface of a microsphere. It is a value reflecting the level of fluorescence of a population of microspheres labeled with an identical reagent. The person skilled in the art will understand, upon reading of the present disclosure, that other statistical parameters related to fluorescence intensity can be used, such as the mean (or average) fluorescent intensity.

In some embodiments, for each PDF of negative samples (e.g., a histogram), a receiver operator characteristic (ROC) function describing the relationship between threshold values and the rate at which false positives occur is determined. A sample histogram (Panel A) and false positive rate curve (Panel B) are shown in FIG. 1. As later explained with reference to FIG. 3, an acceptable rate of false positives will be selected, and the MFI threshold will be determined from the false positive rate curve. The false positive rate curve is determined from the histogram of negative sample MFIs as follows. A series of candidate threshold values is initially selected. At each threshold value, the number of total negative samples with an MFI exceeding that threshold value is divided by the total number of negative samples and represents the false positive rate for that particular threshold. Stated with other words, the false positive rate curve is equivalent to 1−CDF (where CDF refers to the cumulative density function of the negative samples). The CDF is determined by integrating the PDF.

In particular, the PDF of negative samples is used to determine for each at least one signature a false positive rate curve to then select a false positive rate on the false positive rate curve. A false positive criterion is established and a threshold for that signature is determined as a point at which the false positive rate curve intersects the false positive criterion.

The systems and methods according to the present disclosure can be used with any assay with a region of linear response where the measurement taken during the assay varies with concentration of the agent. In some embodiments, the assay can be a multiplexed PCR diagnostic assay using liquid array detection which can be performed, for example, to simultaneously detect viruses and/or other pathological agents, such as agents that, although different, cause clinical signs in animals that are indistinguishable. An example of this assay will be described in Step 1 of the examples section, where a multiplexed PCR assay is performed to detect Foot and Mouth Disease (FMD).

Exemplary data analysis methodology for characterizing the performance of individual signatures is illustrated with reference to the exemplary procedure of the examples section. In those exemplary embodiments, the response of each signature formed by a pair of primers and a probe to negative and virus-spiked clinical samples to evaluate and determine threshold values is characterized.

According to a further embodiment of the present disclosure, the effect of the determined threshold value on the limit of detection (LOD) for at least one signature can be evaluated. The term "limit of detection" as used herein indicates the lowest quantity of a substance that can be distinguished from the absence of that substance with a specific probability. Examples of a limit of detection include the smallest concentration of a virus that can be detected with a probability of detection of 50% or the smallest quantity of DNA template that can be detected with a probability of detection of 75%.

Figure 5:
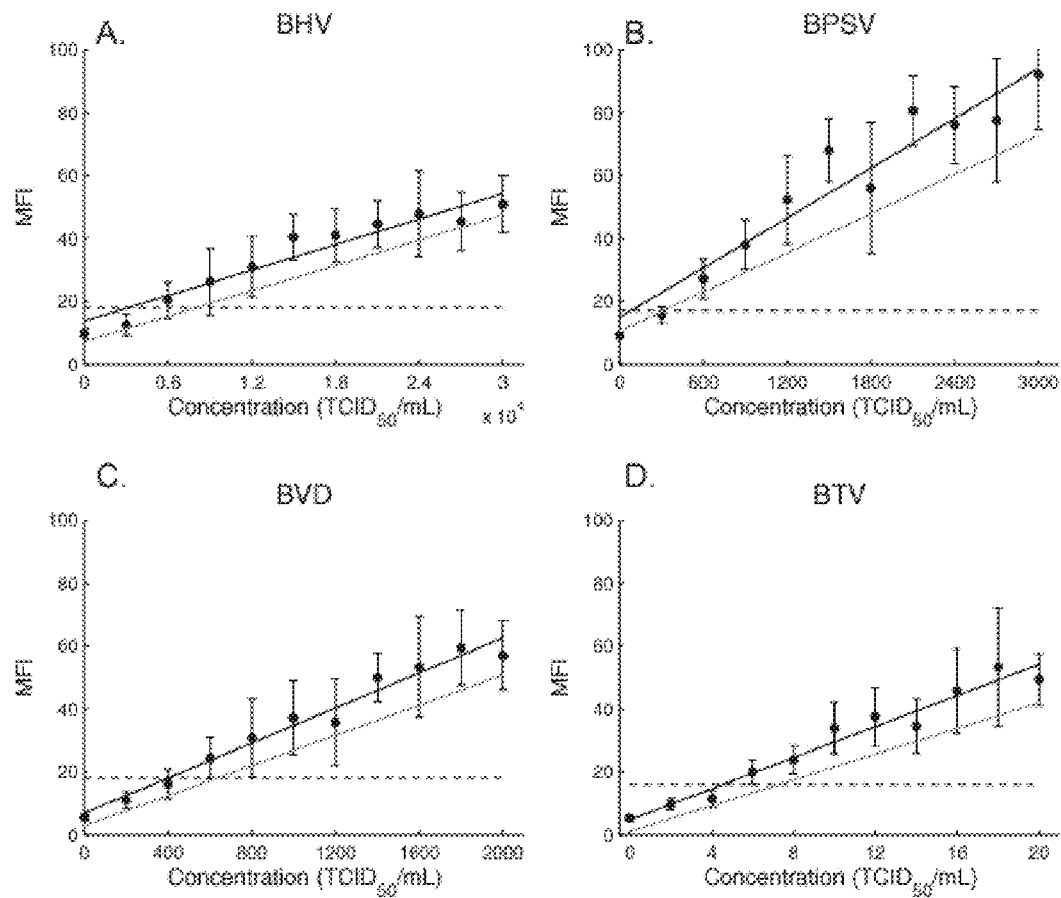
FIG. 5 shows an example of a set of titr$_{ation}$ curves for determining a target concentration associated with a threshold value according to an embodiment of the present disclosure. Panels A-D show calibration curves resulting from high resolution titration assays for the four signatures BHV-3, BPSV-4, BVD-1a, and BTV-2. Each point on the curves represents the mean (n=8) MFI value±1σ. Regression lines (dark solid lines) fitted through the mean values for each signature. The intersection of the regression line with the threshold value (dashed line) indicates the LOD$_{50}$. Intersection of a second regression line (light solid line), fitted through the second smallest MFI value, with the threshold value indicates the LOD$_{87.5}$.

FIG. 5 shows a method for determining the LOD (limit of detection) for each signature according to an embodiment of the present disclosure where the LOD is determined on the basis of the previously found threshold values. Choice of a threshold is a balance between LOD and false positive rate. In particular, when the probability density functions (PDFs) of negative and positive samples overlap (see gray area of FIG. 2), reducing the threshold value results in a lower LOD but increases the false positive rate. On the other hand, increasing the threshold value decreases the false positive rate but increases the LOD.

Figure 3:
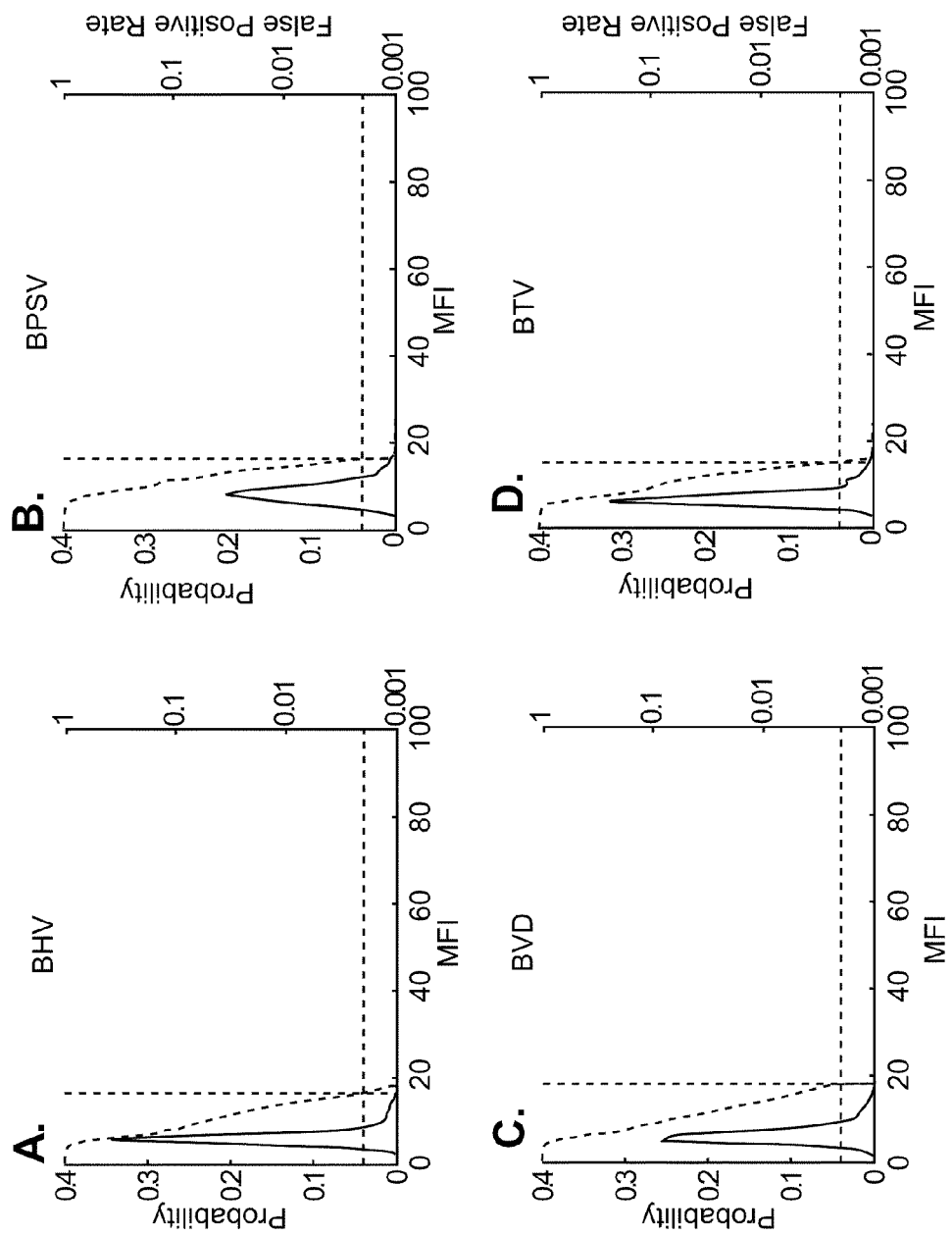
FIG. 3 shows probability density functions of responses (MFI) to negative samples (dark lines) for four signatures (panels A-D) together with their associated FP rate curves (light lines) according to an embodiment of the disclosure. These curves are used to determine the threshold value (vertical dashed line) for each signature at a given FP rate.

To determine the LOD for each signature in accordance with an embodiment of the present disclosure, negative bovine oral swab samples were individually spiked with viable virus over a narrow concentration range. As shown in FIG. 5, linear ($R^2>0.9$) calibration curves were generated for four exemplary signatures by plotting the MFI values (with n=8 in the examples of the figure) versus concentration, as shown by the dark linear regression lines in FIG. 5. The threshold value determined in accordance with the embodiment of FIG. 3 is shown as a horizontal dotted line. The intersection between the calibration curve/regression line and the threshold value represents the $LOD_{50}$, i.e. the concentration of virus that generates an MFI value greater than the threshold value 50% of the time.

By way of example, a second regression line (light line in FIG. 5) was fitted through the second lowest MFI value at each concentration to allow the quantification of LOD an alternate probability of detection. The intersection of particular line and the threshold value represents $LOD_{87.5}$. Both the $LOD_{50}$ and $LOD_{87.5}$ assume the number of replicates (n=8) approximate the variation in MFI responses for each concentration. The distribution of MFI values for a single concentration may be non-Gaussian, which causes the slope of the regression line to vary for each probability of detection.

The person skilled in the art will understand, upon reading of the present disclosure, that the techniques of the present disclosure are not dependent on the response parameter being MFI. In case of a different parameter, calibration curves of that parameter versus concentration will be generated and then the desired LOD of the signature will be determined as the intersection of the calibration curve and the threshold value of the signature.

In several embodiments, methods of calculating thresholds and determining limits of detection in multiplexed biological assays can be performed by carrying out an experimental protocol and a quantitative procedure for analyzing the experimental data obtained by the experimental protocols.

According to a further embodiment of the present disclosure, a method for determining assay performance is disclosed. In particular, the method for determining assay performance according to the present disclosure is based on the previously determined threshold and LOD values.

Figure 7:
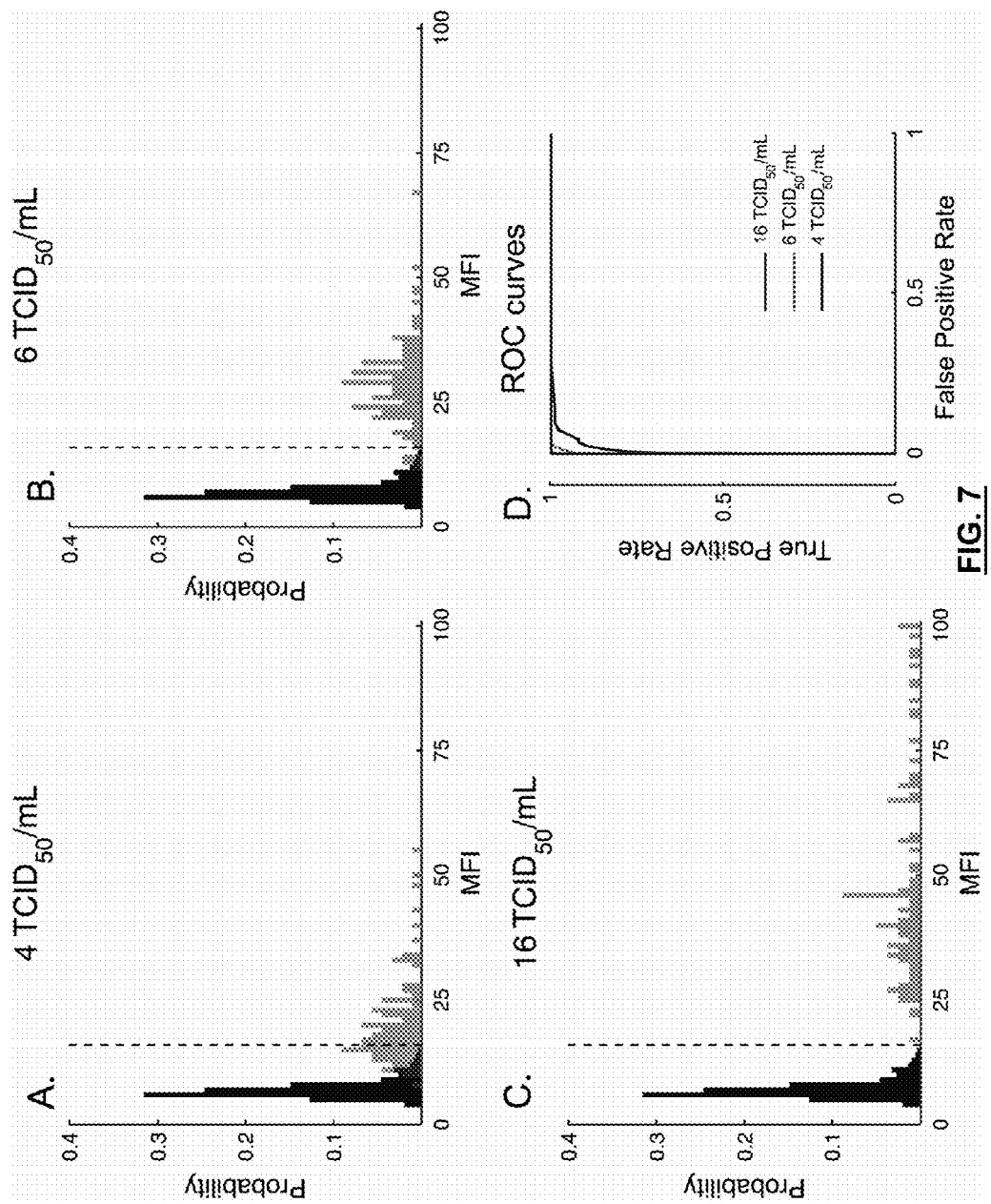
FIG. 7 shows a signature positive response distribution according to an embodiment of the present disclosure. Panels A-C show histograms of bluetongue signature (BTV-2) response (MFI) to negative samples (dark bars, n=1072) and virus spiked samples (light bars, n=88, 4, 6 and 16 TCID$_{50}$/mL). Single-graph ROC curves (panel D) reflect the improved performance of the signature at higher virus concentrations.

As shown in Panel D of FIG. 7, single-graph ROC curves can be constructed by plotting a false positive rate vs true positive rate as the threshold value is varied. The area under the single graph-ROC curve has been used as a measure of assay performance [see reference 16]. However, this measure is subject to bias resulting from its dependence on virus concentration in the sample.

Figure 8:
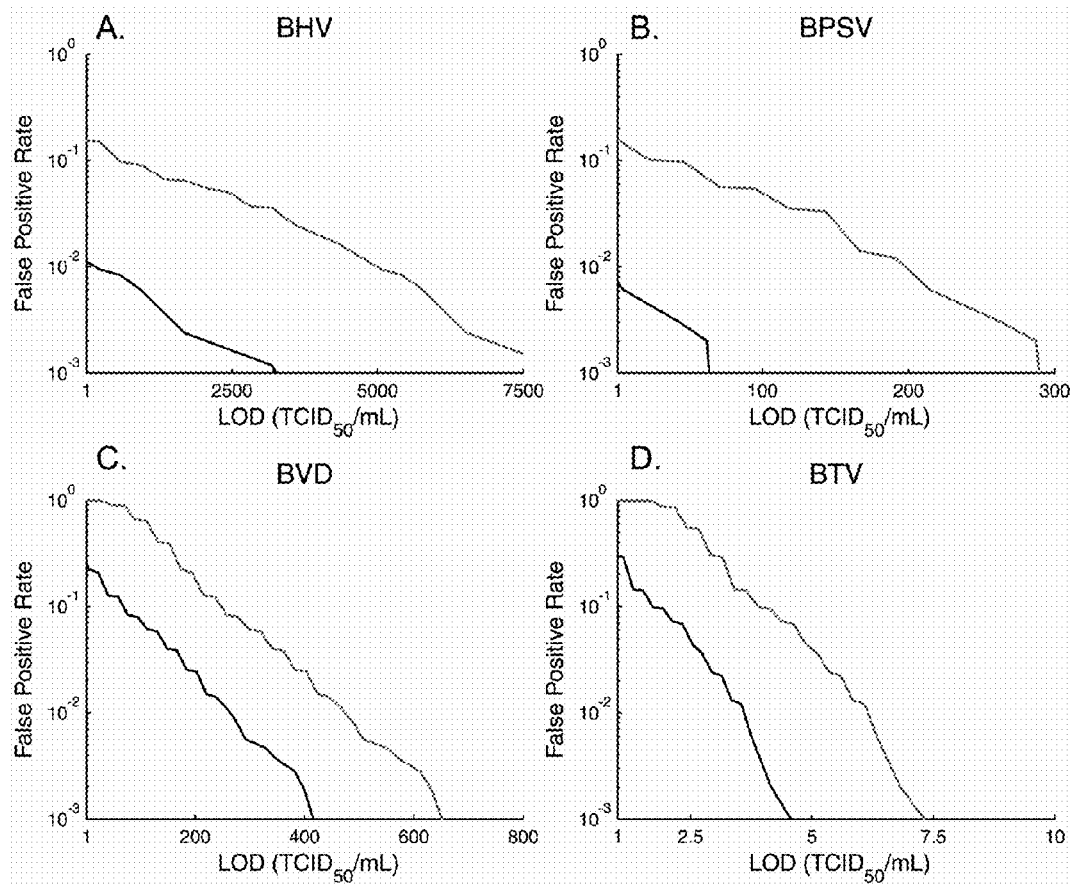
FIG. 8 shows a false positive rate curve for determining a limit of detection according to an embodiment of the present disclosure. Panels A-D show plots of false positive rates versus LOD for four signatures (BHV, BPSV, BVD, and BTV) at a given probability of detection (black line=50%, green line=87.5%).

According to the present disclosure, a different method of determining assay performance is provided. In particular, once the relationship between threshold value and false positive rate has been established (FIG. 3), threshold value is converted to LOD (e.g., $LOD_{50}$ and/or $LOD_{87.5}$) using calibration functions (FIG. 5). A plot of false positive rates versus LOD is then generated, as shown in Panels A through D of FIG. 8. These curves illustrate the increase in LOD as false positive rate decreases. The selection of a particular false positive rate on one of the diagrams of FIG. 8 determines the threshold value for each signature, which in turn, specifies the LOD for each signature.

Incorporating the calibration data ensures that the apparent performance of each signature is not biased by a single concentration of virus. The choice of whether to use the traditional ROC curve of panel D of FIG. 7 or the method according to the present disclosure to characterize assay performance depends upon the nature of the positive samples. If the virus concentration of a positive sample were unknown, as is often the case with clinical samples, the single graph ROC curves would be more appropriate. However, if the assay characterization is conducted using positive samples of known concentration, then including the LOD parameter (Step 6 of the examples section) better accounts for the effect of threshold value selection on performance.

The methodology of the present disclosure can be used to quantify the performance and limitations of all micro array based assays, in particular those performed using the Luminex suspension array. As the Luminex platform is a laboratory instrument used frequently for performing bioassays, there are many potential uses in bio-agent related analysis, medical clinical diagnostics, and analysis of agricultural samples. The process might be generalized and applied to any assay using a flow cytometer during which a median fluorescent intensity (or other statistical measure including mean for example) is determined.

Further advantages and characteristics of the present disclosure will become more apparent hereinafter from the following detailed disclosure by way or illustration only with reference to an experimental section.

EXAMPLES

The method and system herein described are further illustrated in the following examples, which are provided by way of illustration and are not intended to be limiting. In particular, in the following examples, a further description of the methods of the present disclosure is provided with reference to viral nucleic acid detection. A person skilled in the art will appreciate the applicability of the features described in detail for methods of viral nucleic acid detection to detection of other targets, such as proteins, antigens, eukaryotic or prokaryotic cells, and the like.

In particular, in the following examples, target detection is exemplified in experiments directed to identify Foot and Mouth Disease (FMD). FMD is a highly contagious viral disease of cloven-hoofed animals. Although the US has been free of FMD since 1929, the disease is endemic to parts of the Middle East, Africa, Asia and South America. An FMD outbreak in the U.S. has the potential to severely impact the economy. The 2001 FMD outbreak in the UK cost the tax payer more than US$5 billion [see references 1-3].

Early detection is critical for reducing both the spread of disease and the economic impact of FMD. However, symptomatic diagnosis is confounded by other vesicular diseases, termed "look-alikes", some of which are endemic to regions of the US. At present, a farmer, producer or veterinarian suspicious of FMD, based on their clinical observations, could request a State or Federal veterinarian to collect and submit a sample (usually vesicular fluid, tissue or blood) to the Plum Island Animal Disease Center for testing.

Diagnosis of the index case requires confirmatory laboratory testing using techniques such as virus isolation, antigen ELISA, polymerase chain reaction (PCR), and sequencing, which can take at least several days to complete. In the event of positive confirmation of FMD, the Federal government may authorize foot-and-mouth disease virus (FMDV) testing at regional veterinary diagnostic laboratories. For samples confirmed negative for FMD, State or Regional laboratories typically conduct an investigation for FMD look-alike diseases.

Molecular diagnostics, primarily real-time reverse transcriptase polymerase chain reaction (RT-PCR) assays, enable rapid detection of FMDV [see references 4-8], as well as FMDV look-alikes including bovine viral diarrhea virus (BVDV) [see references 9-11], bluetongue virus [see references 12 and 13] and parapoxviruses [see reference 14]. Multiplexing of real-time RT-PCR assays is limited by the broad emission spectra of the fluorescent probes and commercial instruments typically offer four discrete optical channels or less. Testing for FMD and look-alike diseases using conventional real-time PCR requires each disease-specific assay to be run individually. Demand for instrumentation and reagents can often exceed laboratory capacity. Combining individual assays into a single multiplexed diagnostic test that simultaneously differentiates FMD from look-alike diseases could provide a means of rapid, cost-effective viral identification for suspect samples, and could enable early detection if used for routine or targeted surveillance.

According to an example of the present disclosure, a multiplexed RT-PCR liquid array assay for the simultaneous detection and differentiation of FMD virus from other vesicular diseases that induce clinical signs in animals that are similar to FMD was prepared. The assay comprises seventeen signatures, each consisting of a forward primer, reverse primer and probe targeting specific genomic sequences, that test for seven diseases and incorporates four internal controls.

The multiplexed liquid array assay of the present disclosure tests for the presence of nucleic acids from viruses which cause FMD and six look-alike vesicular diseases, including swine vesicular disease, vesicular exanthema of swine, bovine viral diarrhea, bluetongue, parapoxvirus and bovine herpes-1 (also known as infectious bovine rhinotracheitis). Nucleic acids for both DNA and RNA viruses were first purified using a commercially available magnetic bead-based extraction kit then amplified by RT-PCR amplification. The assay comprises seventeen primer-probe sets (i.e., signatures), enabling multi-loci detection of all diseases except bovine viral diarrhea. In contrast to real-time PCR, the liquid array functions as an end-point detector of specific PCR products after thermal cycling is complete. The PCR product was hybridized to signature-specific oligonucleotide-functionalized microspheres, labeled with the fluorescent reporter SAPE, then analyzed using a Bio-Plex flow cytometer to generate a response. The median fluorescence intensity (MFI) was the response parameter selected for use with this assay. The MFI increased with virus concentration, but typically plateaued at high concentrations. This assay is semi-quantitative over a limited range.

Although the data presented herein were acquired using a PCR-based liquid array assay intended for foot-and-mouth disease detection and rule-out, the method should be applicable to other panels of signatures or different assay formats such as immunoassay or serology. Refinements to the methods outlined may be required depending on the application and the type of data acquired. Some considerations are outlined below.

True negative samples may generate MFI values that do not fit a Gaussian distribution and would be considered outliers by a Grubbs' outlier test [see reference 17]. Removal of outliers from data sets used to establish threshold values could lead to higher false positive rates when analyzing unknowns. Their inclusion could result in a higher threshold value and lead to a significant increase of the LOD. The level of compromise between false positive rate and LOD will depend upon the level of performance deemed acceptable, or the assay's "fitness for purpose". If the multiplexed assay was used as a screening tool, lower threshold values may be appropriate, while additional thresholds akin to a rating scale may be implemented to manage results. In this case, the magnitude of the MFI response for a given sample may define the subsequent action, such as repeating the analysis or conducting confirmatory assays, including for example, real-time PCR, ELISA, virus isolation and sequencing.

The present assay incorporates multiple loci detection for all but one of the diseases. Multiple loci increase confidence in detection by targeting different genetic regions of a given target. For highly variable pathogens like FMD virus and bluetongue, which have seven and twenty-four known serotypes respectively, a single PCR-based assay may not detect the gene sequence of interest in all samples. Multiplexed, multiple loci assays significantly increase the probability that one or more signatures will detect the presence of the pathogen providing broader "coverage" of the genetic diversity. With this in mind, higher false positive rates may be acceptable for certain signatures if the overall interpretation is based on the cumulative results for a given target. A detection algorithm would need to need to take into account many factors, such as signature design, sensitivity to target strains and specificity against near neighbors. Furthermore, different sample matrixes may result in different MFI distributions for negative samples and require threshold values to be re-evaluated. Intra- and interlaboratory variation can also influence the magnitude of the threshold value.

National surveillance networks are currently evaluating multiplexed liquid array assays for a range of surveillance applications including foreign animal disease detection and environmental monitoring for bio-threat agents. Users of liquid array technology require data analysis methods to analyze and interpret the results of their multiplexed assay results. The methodology presented enables the user to translate raw responses from liquid array assays to performance characteristics such as false positive rate, false negative rate and LOD and understand the relationship between them. When presented in these terms, the user can better assess the assay's fitness for purpose and provide decision makers with science-based actionable information.

Step 1: Multiplexed Liquid Array Assay

The multiplexed liquid array assay described in this example tests for the presence of nucleic acids from viruses which cause FMD and six look-alike vesicular diseases, including swine vesicular disease, vesicular exanthema of swine, bovine viral diarrhea, bluetongue, parapoxvirus and bovine herpes-1 (also known as infectious bovine rhinotracheitis). Nucleic acids for both DNA and RNA viruses were first purified using a commercially available magnetic bead-based extraction kit then amplified by RT-PCR amplification. The assay comprised seventeen primer-probe sets (i.e., signatures), enabling multi-loci detection of all diseases except bovine viral diarrhea. In contrast to real-time PCR, the liquid array of this example functions as an end-point detector of specific PCR products after thermal cycling is complete. The PCR product was hybridized to signature-specific oligonucleotide-functionalized microspheres, labeled with the fluorescent reporter SAPE, then analyzed using a Bio-Plex flow cytometer to generate a response.

Bovine oral swab samples were collected by a veterinarian from healthy dairy cattle at a commercial dairy (Davis, Calif.), placed individually in vials containing viral transport medium (VTM, 3 mL, Teknova), then stored at −80° C. prior to use. Samples were spiked with infectious viruses including bovine viral diarrhea virus (BVD, Type 1a, Singer strain), bluetongue virus (BTV, Type 2), bovine herpes virus-1 (BHV), and bovine papular stomatitis virus (BPSV) purchased from the USDA National Veterinary Services Laboratory (Ames, Iowa). Virus stocks were received in cell culture supernatant and used without further purification or separation.

Viral DNA and RNA were purified using the MagMAX™-96 Viral RNA Isolation Kit (Ambion, 1836) per the kit instructions with minor modifications. To each well of a 96-well plate, lysis/binding solution (130 μL) and sample (50 μL) were added, then shaken (Lab-line Orbital Shaker, VWR) for 1 min. Bead suspension (20 μL) was added, shaken for 5 min to adsorb nucleic acids, then the beads were captured by placing the 96-well plate on a magnetic ring stand (Ambion, Cat #10050) for 4 min after which the supernatant was removed. The beads were washed sequentially with two different proprietary aqueous-alcohol solutions. The first wash solution (150 μL) was added, shaken for 1 min, the beads captured for 2 min, then the supernatant removed. This step was repeated using the second wash solution. The beads were dried by shaking for 2 min. Elution buffer (50 μL) was added, the 96-well plate was heated to 100° C. for 5 min on digital heat block, (solution temperature reached 65 degrees after 5 min), removed from the heater then shaken for 3 min. The beads were captured for 1 min and the eluent transferred to a clean 96-well round-bottom plate. An aliquot of the purified sample (5 μL) was used for the RT-PCR.

For Multiplex RT-PCR amplification, SuperScript™ III One-Step RT-PCR System with Platinum® Taq DNA Polymerase (Invitrogen, Cat #12574-026) was used. The reaction volume of 25 μL was comprised of nuclease-free water (1.95 μL), primer mix (3.6 μL), SuperScript™ III 2× reaction mix (12.5 μL), $MgSO_4$ (0.95 μL, 50 mM, Invitrogen), SuperScript™ III Platinum Taq polymerase (1 μL) and sample (5 μL). The primer mix contained biotinylated forward primers and unmodified reverse primers for all seventeen signatures plus an internal control After assembly of the reaction, the final concentrations of all primers and $MgSO_4$ were 0.4 μM and 3.5 mM, respectively. All oligonucleotides (Integrated DNA Technologies) were HPLC-purified prior to use.

The RT-PCR thermal cycling protocol used was 55° C. for 30 min, 95° C. for 2 min, then 35 cycles of 95° C. for 15 s, 60° C. for 30 s, and 72° C. for 15 s, followed by 72° C. for 2 min with a final 4° C. hold.

For PCR product-probe hybridization, PCR product (1 µL) was added to a mixed suspension of probe-conjugated Luminex microspheres (22 µL) in a 96-well plate, then placed in a thermal cycler and subjected to 95° C. for 2 min, 55° C. for 5 min, followed by a 4° C. hold for hybridization. Tris-NaCl buffer (100 µL, 0.1 M Tris, 0.2 M NaCl, 0.05% v/v TritonX-100, pH=8.0, Teknova) was added then the suspension was transferred to a 96 well vacuum filter plate (MABVN 1250 Multiscreen Filter Plate, Millipore). The suspension was vacuum-aspirated, and washed twice with Tris-NaCl buffer (2×100 µL). The fluorescent reporter streptavidin phycoerythrin (SAPE, 50 µL, 3 µg/mL) was added then incubated in the dark for 5 min. The suspension was vacuum-aspirated, washed once with Tris-NaCl (100 µL), resuspended in Tris-NaCl (100 µL) then transferred to a 96-well round bottom plate for fluorescent detection on a Bio-Plex Workstation (Bio-Rad, CA) set to count a minimum of 100 events per microsphere class in a 50 µL sample size.

Experiments with viable viruses were conducted using Biosafety Level-2 laboratory space and procedures. Consumables (filtration plates, pipette tips, tubes, etc.) generated during these experiments were handled and disposed of in accordance with the regulations of the local, State and Federal Governments. Personal protective equipment was worn, including gloves, lab coat and goggles.

Step 2—Obtaining a Signature Negative Response Distribution

The PCR product hybridized to the signature-specific oligonucleotide-functionalized microspheres indicated in Step 1 was analyzed to identify a threshold value. The median fluorescence intensity (MFI) was the response parameter selected for use with this assay.

In particular, negative bovine oral swab samples (n=171) were analyzed using the multiplex assay of Step 1 to characterize the negative sample PDFs for each signature. A larger number of negative samples would yield a more representative distribution and increase the resolution of the false positive rate. This could be achieved by collection and analysis of additional true negative samples. However, a large number of negative samples (1072) spiked with a single virus target were also analyzed for the purpose of this study. When a subset of signatures tested positive due to the presence of the corresponding target virus, the results generated by the remaining signatures could be considered as negative data.

In order to analyze the results of the assay of Step 1, raw data exported from the Bio-Plex instrument were imported into MATLAB (MathWorks) then analyzed using a custom program. In particular, the custom program imported MFI data collected with a BioPlex® instrument. After the negative sample data was imported, their MFI values for a given signature were sorted from low to high and assigned a fractional ranking (equivalent of dividing the ranking by the total number of samples). The false positive rate at a particular MFI threshold was equivalent to 1 minus the fractional ranking for that MFI value. Standard Type I linear regression was used. All error bars represent ±1 standard deviation ($\sigma$) of the mean.

The mean response from true negative samples (n=171) and virus positive samples (n ranged between 671 and 895) were not significantly different (p>0.05, student's t test) for all signatures in the multiplex assay of Step 1. These findings indicated that cross-reactivity was negligible for all signatures. Therefore, we used data from negative and virus spiked negative samples for setting threshold values.

Step 3—Determining a Threshold Value Based on a Selected False Positive Rate

Applicants characterized the response of each signature to negative and virus-spiked clinical samples to evaluate and determine threshold values.

The seventeen signatures that comprised the multiplex assay were treated individually for data analysis purposes, whereby each signature was assigned a distinct threshold value. Upon completion of the Bio-Plex analysis, the MFI value for each signature was compared to its respective threshold value to determine whether a given sample should be reported as positive or negative. A signature was considered positive when the numerical value of the MFI was greater than that of the threshold value.

Figure 2:
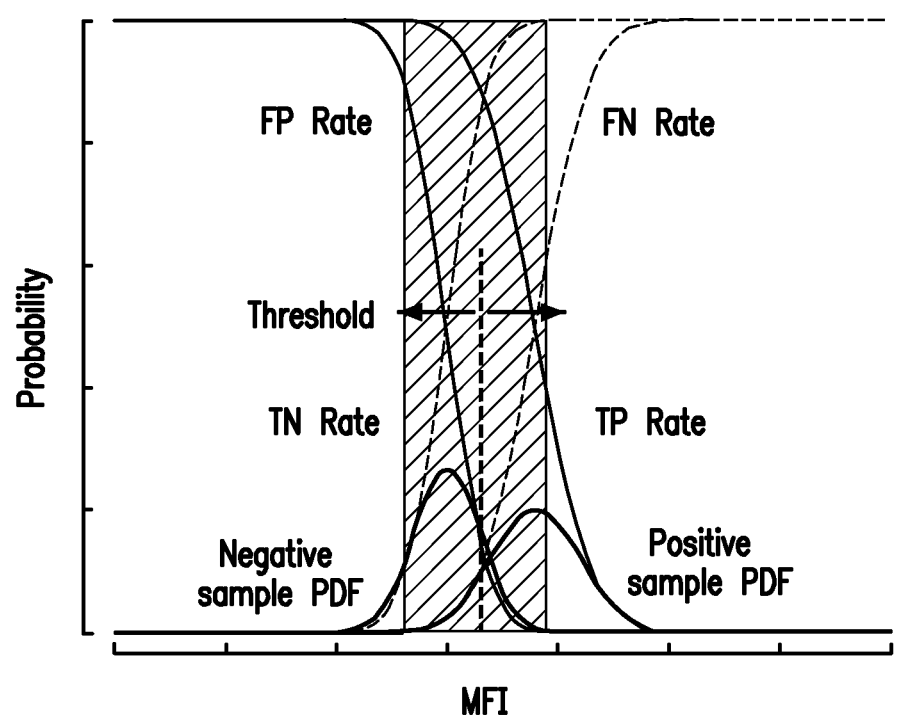
FIG. 2 indicates a schematic diagram of the relationship between an MFI threshold and false positive (FP) and true positive (TP) rate. MFI responses for each signature are plotted as probability density functions (PDFs). The gray rectangular area indicates the region where negative and positive sample PDFs overlap.

Each signature within the multiplex liquid array assay of Step 1 generates a range of responses (MFI) to both negative and positive samples. The distributions of responses obtained from the analysis of both negative and positive samples can be plotted as probability density functions (PDFs) (FIG. 2). Threshold values are typically set in the region where negative and positive sample PDFs overlap, which results in a compromise between the corresponding false positive (FP) and true positive (TP) rates.

FIG. 2 provides a graphical illustration of overlapping negative and positive sample PDFs, showing the relationship between threshold value and the associated FP, TP, true negative (TN), and false negative (FN) rates. Increasing the threshold value decreases the FP and TP rates. FP and true negative (TN) rates sum to one and can be used interchangeably. The same applies for false negative (FN) and TP rates.

Negative sample PDFs for four of the seventeen signatures are shown in FIG. 3 (dark lines). A false positive rate curve (FIG. 3; gray lines) was derived from each negative sample PDF (between 842 and 1066 negatives samples for each signature of interest) and overlaid on each plot. These curves are used to determine the threshold value (FIG. 3; vertical dashed line) for each signature at a given FP rate (e.g. 0.002, FIG. 3; horizontal dashed line).

When, for example, a false positive rate of 0.002, was selected, the corresponding threshold values ranged from 15 to 20 MFI units. The threshold value is the point at which the false positive rate curve intersects the false positive criterion. For FIG. 3, note that the ordinate for the probability of a given MFI value is linear while the abscissa is logarithmic.

Step 4—Determining a Limit of Detection for a Signature Based on a Target Concentration Associated with a Threshold Value Once the threshold level above which an MFI signal is ruled positive has been established (for example, by the procedure of Step 3), quantitative measures of the limit of detection can be calculated by titrating against DNA template for each DNA signature (if a PCR-based assay) or titrating an antigen (if antibody-based assay) for each capture/detector antibody pair. For this low-resolution calibration assay, a wide range of concentrations (scaled logarithmically) is used so that the gross approximation of the limit of detection ($LOD_{approx}$) can be determined.

Figure 4:
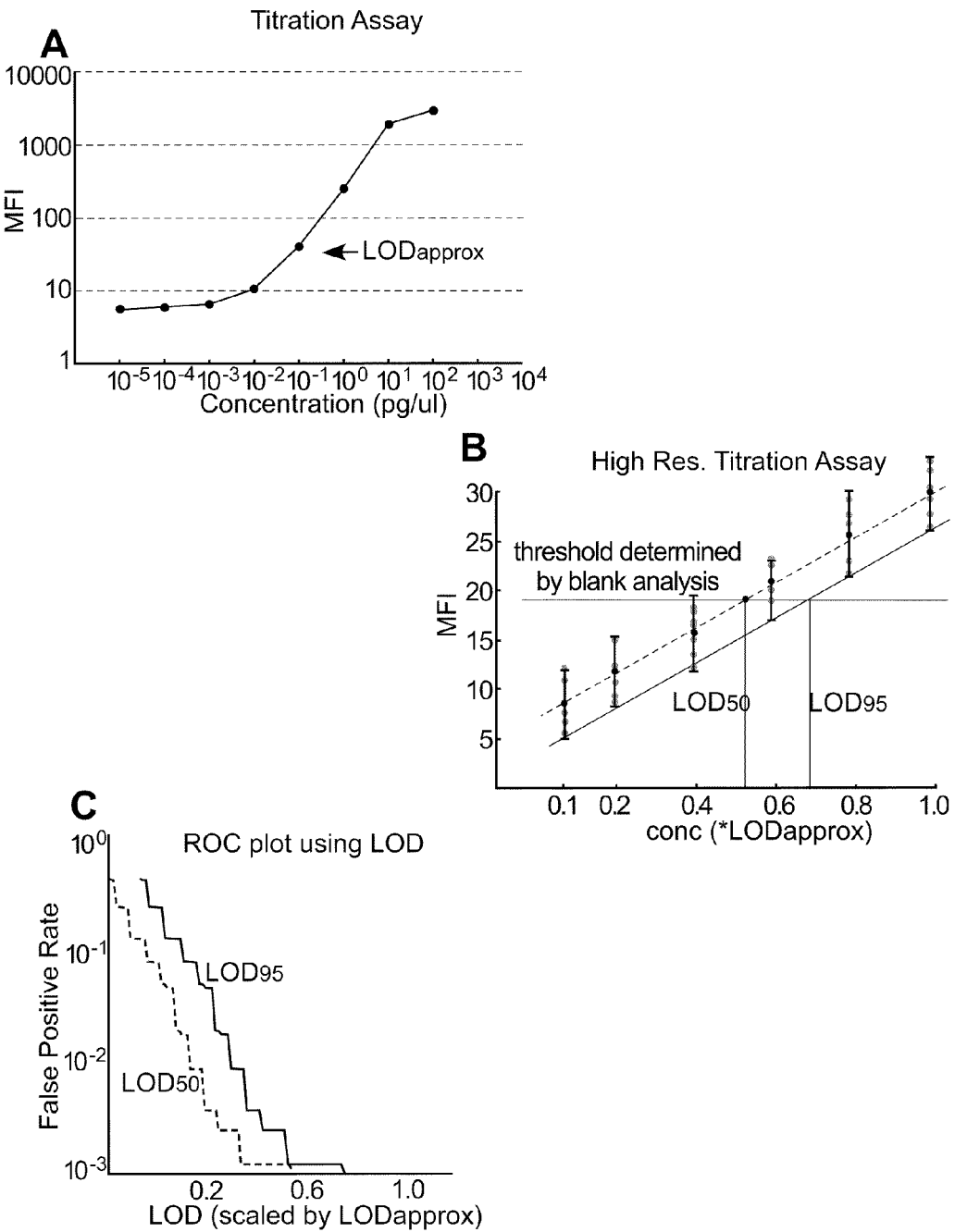
FIG. 4 shows an example of a set of titration curves for determining a target concentration associated with a threshold value, and a false positive rate curve for determining a limit of detection according to an aspect of the present disclosure. Panel A shows an example of a low resolution titration assay, where MFI values for of the indicated concentration (scaled logarithmically) of DNA template (if a PCR-based assay) or antigen (if antibody-based assay) for each signature are plotted. Panel B shows a high resolution titration assay, where MFI values for each concentration (DNA or antigen) surrounding the $LOD_{approx}$ (approximate limit of detection) are plotted. The best fitting straight line through the average MFI values for each concentration is then calculated and plotted (indicated by the darker dashed line in Panel B). Panel C shows ROC curves for the false positive rate plotted against both $LOD_{50}$ and $LOD_{95}$.

In the low resolution calibration assay according to this example, each point in this titration curve may represent the average value of a minimum of two measurements at each concentration. A sample titration curve with $LOD_{approx}$ is shown in FIG. 4A. $LOD_{approx}$ is the first concentration for which the corresponding MFI value is above the threshold level.

Once the $LOD_{approx}$ is determined, the MFI values for a second titration curve covering a much narrower range of concentrations are experimentally determined. In this "high resolution" titration assay, the number of replicates for each concentration is increased, so that standard deviations about the mean values for that concentration can be calculated. The result of this methodology generates a high-resolution calibration function.

FIG. 4B shows an example high-resolution titration assay. A regression line (black dashed lines) fitted through the mean MFI values for a particular signature is shown. The concentration value for which this line intersects the threshold line is referred to as the $LOD_{50}$. The $LOD_{50}$ is defined as the concentration level that will produce MFI values above the threshold level 50% of the time. A second line is fit to the mean MFI values minus a standard deviation (FIG. 4B, gray dashed line). The point where this line intersects the threshold line is the $LOD_{95}$, defined as the concentration value, for which 95% of the MFI values will exceed the threshold level. The $LOD_{50}$ and $LOD_{95}$ serve as two separate measures of the ability of a given assay to detect an antigen/template.

The threshold value acquired according to the method of Step 3 was used to determine the limit of detection (LOD) for each signature. When the PDF (exemplified in FIG. 2) of negative and positive samples overlap, reducing the threshold value results in a lower LOD but increases the false positive rate. Increasing the threshold values increases the LOD but decreases the false positive rate. To determine the LOD for each signature, negative bovine oral swab samples were individually spiked with viable virus over a narrow concentration range. Calibration curves generated by plotting the mean (n=8) MFI values (±1 standard deviation) versus virus concentration (FIGS. 5A-D) were linear ($R^2$>0.9).

FIG. 5, panels A-D, shows regression lines (black lines) fitted through the mean MFI values resulted in $R^2$ values of 0.92, 0.91, 0.97 and 0.95 for signatures BHV-3, BPSV-4, BVD-1a, and BTV-2 respectively. The point at which the regression line intersects the threshold value is the $LOD_{50}$. The $LOD_{50}$ is the concentration of virus that generates an MFI value greater that threshold value 50% of the time. A second regression line was fitted through the second lowest MFI value at each concentration to allow the quantification of LOD at an alternate probability of detection. The intersection of this second line and the threshold value is the $LOD_{87.5}$.

In the example of FIGS. 5A-D, the intersection of the regression line (black line) with the threshold value (dashed red line) indicates the $LOD_{50}$. Intersection of a second regression line (blue line), fitted through the second smallest MFI value, with the threshold value indicates the $LOD_{87.5}$. Both the $LOD_{50}$ and $LOD_{87.5}$ assume the number of replicates (n=8) approximate the variation in MFI responses for each concentration. The distribution of MFI values for a single concentration may be non-Gaussian, which causes the slope of the regression line to vary for each probability of detection, as exemplified in FIGS. 5A-D.

Step 5—Quantifying Performance of a Signature by Obtaining a Signature Positive Response Distribution at the Limit of Detection Responses from positive samples can overlap with those acquired from negative samples. This is shown in FIG. 6A, where a histogram of the MFI values resulting from assays with a single chosen concentration ($LOD_{50}$ for FIG. 6A) is plotted in a manner identical to that done in Example 2.

In particular, after performing the titrations of Step 4, a number of samples are run for a single concentration (i.e. the $LO_{D50}$) of a single template (or antigen). A histogram of the MFI values resulting from the assays with the single chosen concentration is plotted in a manner identical to that done for the blanks (i.e., measurements taken from negative samples) (FIG. 6A). As the threshold increases, the percentage of blanks with MFI values above threshold and the percentage of samples with template with MFI values above threshold will vary. The former yields the false positive rate while the latter yields a true positive rate. These two measures of the assay's selectivity and sensitivity can be plotted as an ROC curve (FIG. 6B). This curve illustrates the effect that selecting a threshold has on the trade-off between the true and false positive rates for a given concentration of template.

The amount of overlap is dependent on the virus concentration in the sample. Using a single bluetongue signature as an example, data from negative samples (n=1072) and virus spiked samples at three different concentrations close to the LOD (4, 6 and 16 $TCID_{50}$/mL) were plotted together as histograms. As the virus concentration increased, the amount of overlap between the distributions decreased. This is shown in FIG. 7, where panels A-C show histograms of bluetongue signature (BTV-2) response (MFI) to negative samples (blue bars, n=1072) and virus spiked samples (red bars, n=88, 4, 6 and 16 $TCID_{50}$/mL). The latter histogram represents the signature positive response distribution.

Single-graph ROC curves were constructed by plotting the false positive rate vs. the true positive rate as the threshold value was varied (FIG. 7D, and further exemplified in FIG. 6B). The area under the single-graph ROC curve has been used as a measure of assay performance [see reference 16]. However, this measure is subject to bias resulting from its dependence on virus concentration in the sample. FIG. 7D reflects the improved performance of the signature at higher virus concentrations using the single-graph ROC curve method.

Figure 6:
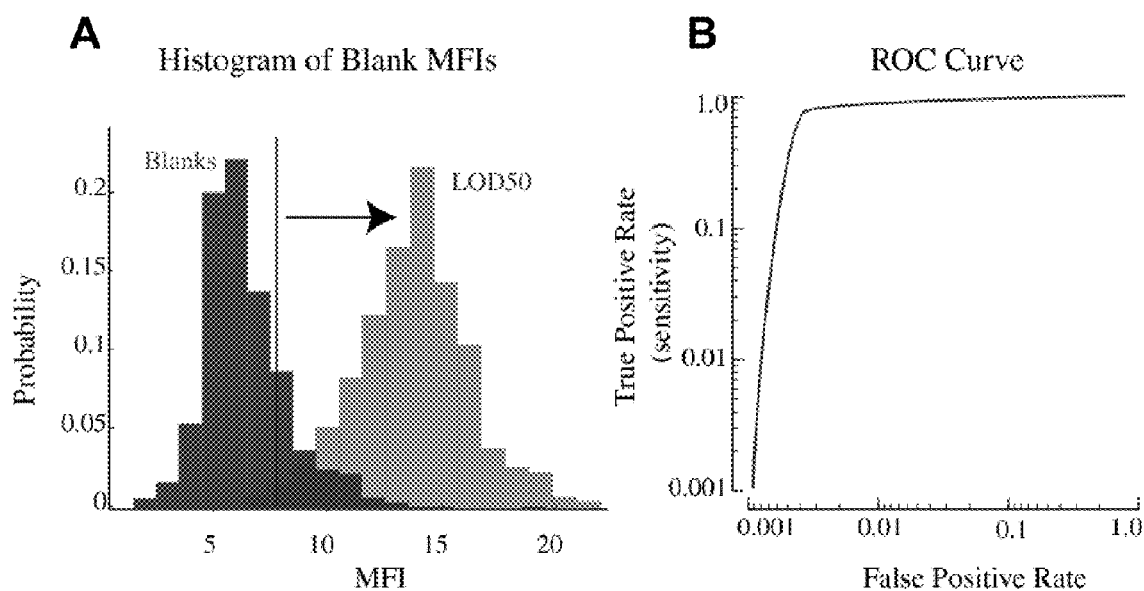
FIG. 6 shows a signature positive and negative response distribution and a false positive rate curve for determining a limit of detection according to an embodiment of the present disclosure. In particular, Panel A shows a histogram of the MFI values resulting from the assays with a single chosen concentration of DNA or antigen plotted in a manner identical to that done for the blanks (i.e., measurements from negative samples). Panel B shows the false positive rate plotted against the true positive rate in the form of a ROC curve.

The above described Step 4 shows the steps for determining the limit of detection at a given probability of detection. The generation of the ROC curve in FIG. 6 is a means of describing the assay performance (in terms of false positive and false negative rate) at a particular concentration (which may or may not represent the limit of detection for a particular probability of detection). A parameter that is frequently derived from the ROC curves that is used to quantify the performance of the assay is the area under the curve (AUC) which will increase from 0.5 to 1 as assay performance improves.

Incorporating the high-resolution calibration data of Step 4 ensures that the apparent performance of each signature is not biased by a single concentration of virus. The choice of whether to use the traditional ROC curve of the present Example or the method of Step 6 (detailed below) to characterize assay performance depends upon the nature of the positive samples. If the virus concentration of a positive sample were unknown, as is often the case with clinical samples, the single graph ROC curves would be more appropriate. However, if the assay characterization is conducted using positive samples of known concentration, then including the LOD parameter (Step 6) better accounts for the effect of threshold value selection on performance.

Step 6—Determining a Limit of Detection for a Signature based on a Selected False Positive Rate Plots of false positive rate versus LOD incorporate concentration and serve as an alternative to the single-graph ROC curves described in Step 5. Once the relationship between threshold value and false positive rate has been established, threshold value was converted to a LOD using the calibration function of Step 4.

To derive a LOD, two curves for each signature were generated using $LOD_{50}$ and $LOD_{87.5}$. These curves illustrate the increase in LOD as false positive rate decreases. The selection of a particular false positive rate determines the threshold value for each signature, which in turn, specifies the LOD for each signature.

As exemplified in FIG. 8A-D, changing the false positive rate affects the LOD for each of four signatures (BHV, BPSV, BVD, and BTV) at a given probability of detection (dark line=50%, gray line=87.5%). The desired false positive rate is selected based upon the relative costs (economic or otherwise) of a false positive and false negative result in the assay.

Incorporating the calibration data of Step 4 ensures that the apparent performance of each signature is not biased by a single concentration of virus. The choice of whether to use the traditional ROC curve of Step 5 or the procedure of the present example to characterize assay performance depends upon the nature of the positive samples. If the virus concentration of a positive sample were unknown, as is often the case with clinical samples, the single graph ROC curves would be more appropriate. However, if the assay characterization is conducted using positive samples of known concentration, then including the LOD parameter of the present example better accounts for the effect of threshold value selection on performance.

The examples set forth above are provided to give those of ordinary skill in the art a complete disclosure and description of how to make and use the embodiments of the devices, systems and methods of the disclosure, and are not intended to limit the scope of what the inventors regard as their disclosure. All patents and publications mentioned in the disclosure are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The terms "multiple" and "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. In particular, modifications of the above-described modes for carrying out the disclosure that are obvious to persons of skill in the art are intended to be within the scope of the present disclosure. Accordingly, other embodiments are within the scope of the following claims.

LIST OF REFERENCES (1) Thompson, D.; Muriel, P.; Russell, D.; Osborne, P.; Bromley, A.; Rowland, M.; Creigh-Tyte, S.; Brown, C. Rev. Sci. Tech. Off. Int. Epiz. 2002, 21, 675-687.
(2) Bourn, J. Department for environment, food and rural affairs, National Audit Office, U.K., 2005, pp 1-61.
(3) Kitching, R. P.; Hutber, A. M.; Thrusfield, M. V. Veterinary Journal 2005, 169, 197-209.
(4) Reid, S. M.; Parida, S.; King, D. P.; Hutchings, G. H.; Shaw, A. E.; Ferris, N. P.; Zhang, Z. D.; Hillerton, J. E.; Paton, D. J. Vet. Res. 2006, 37, 121-132.
(5) Zhang, Z. D.; Alexandersen, S. J. Virol. Methods 2003, 111, 95-100.
(6) Callahan, J. D.; Brown, F.; Csorio, F. A.; Sur, J. H.; Kramer, E.; Long, G. W.; Lubroth, J.; Ellis, S. J.; Shoulars, K. S.; Gaffney, K. L.; Rock, D. L.; Nelson, W. M. J. Am. Vet. Med. Assoc. 2002, 220, 1636-1642.
(7) Reid, S. M.; Ferris, N. P.; Hutchings, G. H.; Zhang, Z. D.; Belsham, G. J.; Alexandersen, S. J. Virol. Methods 2002, 105, 67-80.
(8) Oleksiewicz, M. B.; Donaldson, A. I.; Alexandersen, S. J. Virol. Methods 2001, 92, 23-35.
(9) Letellier, C.; Kerkhofs, P. J. Virol. Methods 2003, 114, 21-27.
(10) Bhudevi, B.; Weinstock, D. Vet. Microbiol. 2001, 83, 1-10.
(11) Baxi, M.; McRae, D.; Baxi, S.; Greiser-Wilke, I.; Vilcek, S.; Amoako, K.; Deregt, D. Vet. Microbiol. 2006, 116, 37-44.
(12) Johnson, D. J.; Wilson, W. C.; Paul, P. S. Vet. Microbiol. 2000, 76, 105-115.
(13) Jimenez-Clayero, M. A.; Aguero, M.; Miguel, E. S.; Mayoral, T.; Lopez, M. C.; Ruano, M. J.; Romero, E.; Monaco, F.; Polci, A.; Savini, G.; Gomez-Tejedor, C. J. Vet. Diagn Invest. 2006, 18, 7-17.
(14) Nitsche, A.; Buttner, M.; Wilhelm, S.; Pauli, G.; Meyer, H. Clin. Chem. 2006, 52, 316-319.
(15) Fitch, J. P. Evolutionary Theories of Detection. DHS IEEE Conference, Boston Mass., Apr. 25-28, 2005. UCRL CONF-212194. llnl.gov/tid/lof/documents/pdf/319757.pdf.
(16) Zweig, M. H.; Campbell, G. Clin. Chem. 1993, 39, 561-577.
(17) Barnett, V.; Lewis, T. Outliers in Statistical Data, 2nd ed.; Wiley: NY, 1984.

What is claimed is:

1. A method for determination of threshold values of signatures composing an assay, each signature enabling detection of a target, the method comprising:
   providing an assay, said assay comprising signatures, said signatures enabling detection of a target, and for each signature:
      determining a probability density function (PDF) of negative samples in the assay;
      based on the determined PDF of negative samples, determining a false positive rate curve;
      generating a calibration curve of assay response parameter values versus concentration;
      generating a plot of false positive rate versus the limit of detection (LOD);
      selecting a LOD such that a desired false positive rate is obtained; and
      determining the threshold corresponding to the selected LOD.

2. The method of claim 1, wherein the threshold values are MFI threshold values.

3. The method of claim 1, wherein the signatures are the primer-probe sets comprising a forward primer, a reverse primer, and a probe.

4. The method of claim 1, wherein the target is indicative of a disease.

5. The method of claim 1, wherein the assay is a multiplexed array assay.

6. The method of claim 1, further comprising:
assigning to each signature the determined threshold as a distinct threshold value;
providing a sample; and
for each signature, comparing the sample with that signature to generate positive samples if a sample fluorescence intensity-related parameter is higher than the threshold value for that signature and negative samples if the sample fluorescence intensity-related parameter is lower than the threshold value for that signature.

7. The method of claim 6, wherein the sample fluorescence intensity-related parameter is a median fluorescence intensity (MFI) parameter.

8. The method of claim 6, wherein providing the sample comprises generating a sample response through flow cytometry.

9. The method of claim 6, wherein the target is indicative of a disease.

10. The method of claim 6, wherein the assay is a multiplexed array assay.

11. The method of claim 1, further comprising:
assigning to each signature the determined threshold as a distinct threshold value;
for each signature, generating a calibration curve of fluorescence intensity-related parameter values versus concentration; and
determining a desired LOD of the signature as the intersection value between the calibration curve of the signature and the threshold value of the signature.

12. The method of claim 11, further comprising determining a second LOD in addition to the desired LOD.

13. The method of claim 11, wherein the fluorescence intensity-related parameter values are median fluorescence intensity (MFI) values.

14. The method of claim 1, wherein the false positive rate curve is plotted as false positive rates as a function of threshold values.

15. The method of claim 1 further comprising:
establishing a false positive criterion; and
determining a threshold for the signature as a point at which the false positive rate curve intersects the false positive criterion.

* * * * *